United States Patent
VanRyzin et al.

(10) Patent No.: US 6,828,910 B2
(45) Date of Patent: Dec. 7, 2004

(54) APPARATUS FOR MONITORING GAS CONCENTRATIONS

(75) Inventors: Patrick Allen VanRyzin, Pewaukee, WI (US); Michael J. Palmer, New Berlin, WI (US); Darrell E. Johnson, Elm Grove, WI (US); William James Sheets, Menomonee Falls, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 56 days.

(21) Appl. No.: 10/417,040

(22) Filed: Apr. 16, 2003

(65) Prior Publication Data

US 2004/0207529 A1 Oct. 21, 2004

(51) Int. Cl.7 .............................................. G08B 23/00
(52) U.S. Cl. .............................. 340/573.1; 128/200.24; 340/531; 600/529
(58) Field of Search ............................. 340/573.1, 531; 422/84; 128/200.24; 600/529, 532, 538, 543

(56) References Cited

U.S. PATENT DOCUMENTS

| | | | | |
|---|---|---|---|---|
| 5,159,934 A | * | 11/1992 | Hoberman | 600/532 |
| 5,197,895 A | * | 3/1993 | Stupecky | 439/194 |
| 5,343,869 A | * | 9/1994 | Pross et al. | 600/301 |
| 5,394,881 A | * | 3/1995 | Block, Jr. | 600/529 |
| 5,632,281 A | * | 5/1997 | Rayburn | 600/532 |
| 5,716,380 A | * | 2/1998 | Yerkovich et al. | 607/5 |

* cited by examiner

*Primary Examiner*—Thomas Mullen
(74) *Attorney, Agent, or Firm*—Andrus, Sceales, Starke & Sawall, LLP

(57) ABSTRACT

A patient monitoring system has a patient monitor with a screen and mainstream gas input connector configured to receive a mainstream gas concentration signal from a mainstream gas analyzer. A sidestream gas analyzer has an output connector and is configured to transmit a sidestream gas concentration signal via the output connector. The patient monitor receives the sidestream gas concentration signal via the mainstream gas input connector for display on the screen.

27 Claims, 2 Drawing Sheets

APPARATUS FOR MONITORING GAS CONCENTRATIONS

FIELD OF THE INVENTION

The invention relates to a patient monitor used to monitor gas concentrations. In particular, the patient monitor includes a module that facilitates a conversion from mainstream gas concentration measurement to sidestream gas concentration measurement.

BACKGROUND OF THE INVENTION

Patient monitors are used to monitor and display patient data, typically in a medical setting. Examples of measured parameters may include electrocardiogram data, non-invasive blood pressure, impedance respiration, SpO2, and temperature. Further, patient monitors may be used to monitor the carbon dioxide (CO2) in a patient's breath during a respiratory cycle. Such measurement of carbon dioxide concentration over time is referred to as capnography and is used to assess the adequacy of patient ventilation, patient cardiac function, and other related patient functions.

In general, capnography data is presented on a patient monitor via a wave form or numerical data that displays the carbon dioxide level in the patient's breath, measured in kPa, mmHg, percent, or equivalent dimension. One capnography parameter that is particularly useful is the amount of carbon dioxide at the end of each breath, known as end-tidal carbon dioxide (EtCO2). EtCO2 may be used to calculate an approximate value of carbon dioxide pressure in arterial blood, which provides information as to the patient's cardiovascular and respiratory system functionality.

There are several different ways that the concentration of exhaled carbon dioxide may be measured. Methodologies may include photoacoustic spectroscopy, mass spectrometry, Raman scattering measurement, and infrared absorption spectroscopy (IR spectroscopy). IR spectroscopy is a common method utilizing a light source to transmit a beam of light through a gaseous sample. The light beam has a wavelength that is preferentially absorbed by CO2. The transmitted radiation is measured by a photodetector. The amount of absorbed radiation indicates the concentration of CO2 in the sample volume. A commonly used wavelength for IR spectroscopy when used to measure carbon dioxide concentration is 4.3 microns.

Two types of gas analyzers may be used to measure gas concentrations, such as carbon dioxide. Mainstream gas analyzers are typically located at a patient's airway as part of an adapter directly coupled to the airway of an intubated patient. The adapter is typically proximate the endotracheal tube. As the respiratory gases travel through the patient's airway and the mainstream gas analyzer adapter, the desired gas, such as CO2 may be monitored. A sidestream gas analyzer diverts a portion of the patient's inspired and expired respiratory gases from a patient's airway to be transported to the sidestream gas analyzer for measurement. The analyzed gas sample may be either returned to the patient's circuit or discarded.

Mainstream gas analyzers are typically utilized on intubated patients, who must be fully sedated. A sidestream side analyzer permits the physician to attach a nasal cannula accessory to the patient, avoiding the need to intubate. Further, a sidestream gas analyzer typically has the ability to measure low flow rates, as may be the case with smaller patients. In other circumstances, a mainstream gas analyzer may be desired, such as when an immediate gas concentration reading is desired, as opposed to the delayed response associated with the sample travel time of sidestream gas analyzers.

In certain conventional patient monitors, a port or interface may be provided to accept input signals from a mainstream CO2 analyzer, but a separate module may be required in an auxiliary rack to permit the monitoring and display of data from a sidestream CO2 analyzer. A separate interface or port may be required on the patient monitor for sidestream CO2 analysis. Accordingly, it would be advantageous to have a patient monitor that is adapted to easily receive and display the signals from a mainstream gas analyzer and a sidestream gas analyzer. It would further be advantageous to have a conversion module adapted to permit the user of a patient monitor to easily convert from a mainstream gas analyzer to a sidestream gas analyzer without requiring additional equipment.

It would be desirable to provide a system and/or method that provides one or more of these or other advantageous features. Other features and advantages will be made apparent from the present specification. The teachings disclosed extend to those embodiments that fall within the scope of the appended claims, regardless of whether they accomplish one or more of the aforementioned needs.

BRIEF DESCRIPTION THE INVENTION

One embodiment of the invention relates to a patient monitoring system. The patient monitoring system has a patient monitor with a screen and a mainstream gas input connector configured to receive a mainstream gas concentration signal from a mainstream gas analyzer. The patient monitoring system further includes a sidestream gas analyzer having an output connector, the sidestream gas analyzer configured to transmit a sidestream gas concentration signal via the output connector. The patient monitor receives the sidestream gas concentration signal via the mainstream gas input connector for display on the screen.

The invention is capable of other embodiments and of being practiced or being carried out in various ways. Alternative exemplary embodiments relate to other features and combinations of features as may be generally recited in the claims.

BRIEF DESCRIPTION OF THE DRAWINGS

The invention will become more fully understood from the following detailed description, taken in conjunction with the accompanying drawings, wherein like reference numerals refer to like elements, in which.

DESCRIPTION OF PREFERRED AND OTHER EXEMPLARY EMBODIMENTS

Figure 1:
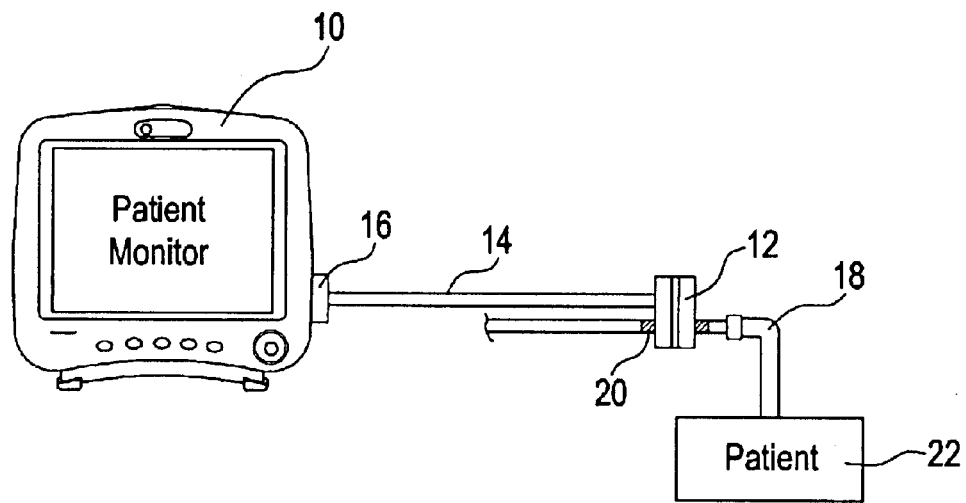
FIG. 1 is a schematic of a mainstream gas analyzer system.

Referring to FIG. 1, in a mainstream gas analyzer system, a patient monitor 10 may be used to display the concentration of a gas component in respiratory gas by utilizing a mainstream gas analyzer 12. The mainstream gas analyzer 12 provides gas concentration data to the patient monitor 10 via a sensor cable 14 that is connected to the patient monitor 10 at an interface, such as a port or connector 16. The mainstream gas analyzer 12 is coupled to the airway 18 of a patient 22 near the patient's end of an external respiratory system via an airway adapter 20. Typically, the patient 22 is on mechanical ventilation via endotracheal intubation when mainstream gas analysis is used.

In an exemplary embodiment, the mainstream gas analyzer 12 measures the concentration of exhaled carbon dioxide ($CO_2$), in particular, end-tidal $CO_2$ ($EtCO_2$). The mainstream gas analyzer 12 may utilize IR spectroscopy to measure the amount of absorption of light by $CO_2$ in the airway, thus determining the $CO_2$ concentration at a particular point in time. The patient monitor 10 then processes the signal (e.g. analog or digital) from the mainstream gas analyzer 12, and displays a waveform and other data associated with the mainstream gas analyzer measurement on a visual display of the patient monitor 10.

Figure 2:
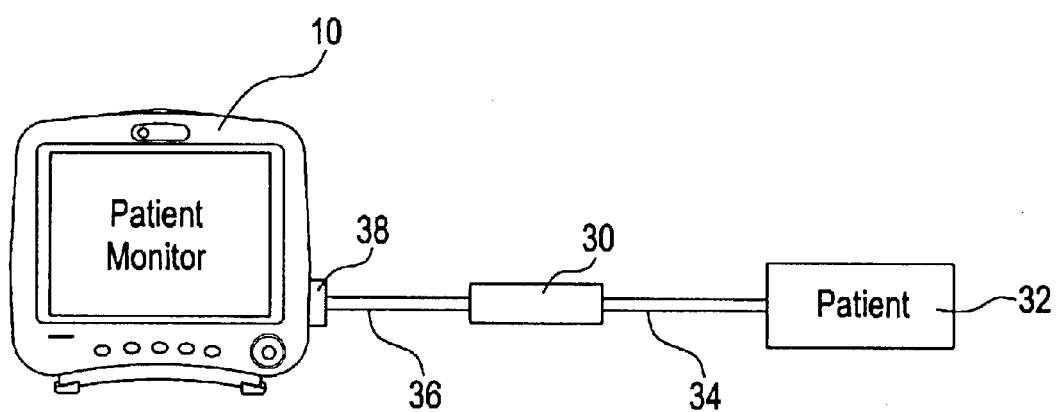
FIG. 2 is a schematic of a sidestream gas analyzer system.

Referring to FIG. 2, a sidestream gas analyzer 30 may be used to measure the concentration of gas components in a sample drawn from the air stream of a patient 32. The sample may be drawn from a patient's endotracheal tube if the patient is intubated, but may also be drawn from a cannula or mask proximate a patient's trachea, such as via a nasal cannula accessory. The gas sample is conveyed to the sidestream gas analyzer 30 by a sample tube 34, which may be a few meters in length and utilize a flow rate in the range of 50–150 ml/min. The sidestream gas analyzer 30 measures gas concentrations, such as the concentration of $CO_2$, utilizing a known measurement method such as IR spectroscopy and provides a signal to the patient monitor 10 via sensor cable 36. The sensor cable 36 may be connected to the patient monitor 10 via a port or connector 38.

Figure 3:
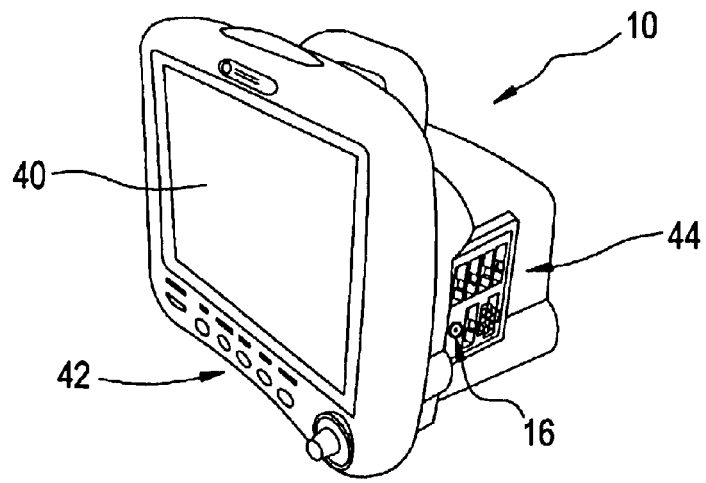
FIG. 3 is a perspective view of a patient monitor.

Referring to FIG. 3, in an exemplary embodiment, patient monitor 10 is a multi-parameter patient monitor available from GE Medical Systems Information Technologies, although the term "patient monitor" is not intended to be limited to any particular brand or type of patient monitor. The patient monitor 10 includes a visual display such as screen 40 and is designed to monitor a set of parameters, including $CO_2$ concentration. A set of controls 42 provides a user interface and a number of input data connectors 44 are provided that serve as inputs for data relating to patient parameters. The $CO_2$ connector 16 is one of the input data connectors 44. As is known in the art, the patient monitor 10 includes logic, such as software, firmware, hard wired circuits, application specific integrated circuits, or other computerized instructions necessary to provide visual output and perform other calculations on the signals provided via connectors 44. In particular, the patient monitor 10 may display capnography data based on $CO_2$ sensor readings, including $EtCO_2$ data. The patient monitor 10 may perform various calculations, calibrations, and compensation functions to provide the desired output. As shown in the system depicted in FIG. 1, in one embodiment a mainstream gas analyzer 12 provides capnography data to patient monitor 10.

Figure 4:
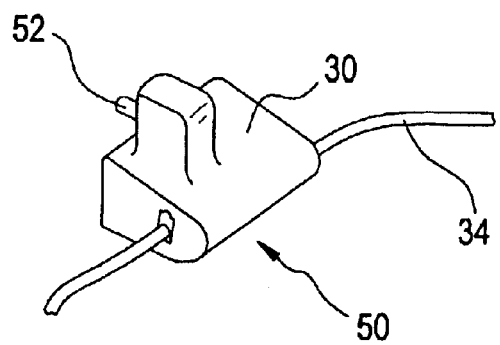
FIG. 4 is a perspective view of a sidestream conversion module.

Referring to FIG. 4, in a preferred embodiment, a module, shown as sidestream conversion module 50 may be connected to sample tube 34. The module 50 includes sidestream gas analyzer 30 used to measure gas concentrations. In one embodiment, sidestream gas analyzer 30 utilizes a photodetector to determine the $CO_2$ concentration in a sample via IR absorption spectroscopy. Data output from the sidestream gas analyzer 30 is sent as a signal (e.g. digital or analog) via a connector such as output plug 52.

Referring to FIG. 2, in certain conventional systems, the signal from sidestream gas analyzer 30 may be sent via a sensor cable 36 to a connector 38 on patient monitor 10 (separate from mainstream input connector 16). In other conventional embodiments, the sensor cable 36 may connect to a separate logic card or module in an auxiliary card rack (not shown) that separately provides data to patient monitor 10. However, referring to FIG. 5 in a preferred embodiment, sidestream conversion module 50 connects directly to patient monitor 10. The connection may be accomplished by plugging output plug 52 into $CO_2$ connector 16. Accordingly, sidestream conversion module 50 permits easy conversion from mainstream gas analysis to sidestream gas analysis using the same connector 16 on the patient monitor 10. Further, sidestream conversion module 50 is directly plugged into patient monitor 10 without the need for sensor cable 36 as shown in the system of FIG. 2.

In an exemplary embodiment, sidestream conversion module 50 is able to provide its data signal directly to the mainstream $CO_2$ connector 16 by emulating the signal provided by mainstream gas analyzer 12. For example, in an analog carbon dioxide measurement device, the output voltage corresponding to various $CO_2$ concentrations would be the same for the sidestream gas analyzer 30 as the mainstream gas analyzer 12. Accordingly, the patient monitor 10 need not differentiate between the input signals provided by either mainstream gas analyzer 12 or sidestream gas analyzer 30 and may receive either input for data analysis and display via a signal connector, in a preferred embodiment, the mainstream carbon dioxide connector 16.

In another exemplary embodiment, patient monitor 10 may include logic that analyzes the signal input via connector 16 and discerns the type of device sending the signal. The logic of patient monitor 10 may then analyze and display the input gas concentration data properly by using an appropriate set of instructions depending upon the type of device sending the signal. In this fashion, signals from mainstream gas analyzer 12 or sidestream gas analyzer 30 may be received via the same connector 16 even if the signal from sidestream gas analyzer 30 does not emulate the signal from mainstream gas analyzer 12.

Sidestream conversion module 50 may be used to effectuate the conversion from mainstream gas monitoring to sidestream gas monitoring depending on the preference of the user of patient monitor 10. Note that in each of the two examples indicating how sidestream conversion module 50 may be used to convert between sidestream monitoring and mainstream monitoring using a single connector on the patient monitor 10, the mainstream carbon dioxide connector 16 is shown as being the single connector used to receive either signal. However, another type of connector may be used to receive each of the signals within the scope of the present invention.

Figure 5:
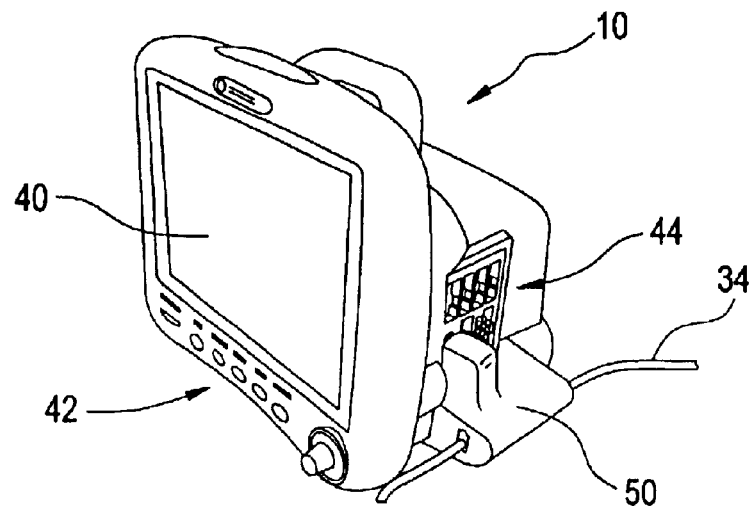
FIG. 5 is a perspective view of a patient monitor having a sidestream conversion module attached.

Further referring to FIGS. 4 and 5, sidestream conversion module 50 attaches directly to patient monitor 10, providing the conversion from mainstream $CO_2$ monitoring to sidestream $CO_2$ monitoring with no additional hardware required. In an exemplary embodiment, the module 50 is intended to function with a number of similarly configured patient monitors having a single $CO_2$ connector. In a preferred embodiment, the patient monitor 10 requires no additional logic, such as software, firmware, or other instructions to monitor, perform calculations on, or display the data provided by sidestream conversion module 50. Instead, sidestream conversion module 50 provides an electronic data signature via output plug 52 that is configured for use by the mainstream gas analyzer 12 via the mainstream $CO_2$ connector 16.

In circumstances in which it may be desirable to utilize sidestream gas analysis instead of mainstream gas analysis, such as when the patient is not intubated, a medical provider may easily convert from mainstream gas analysis, in particular mainstream CO2 gas concentration analysis to sidestream gas analysis, in particular sidestream CO2 concentration analysis, utilizing the same patient monitor hardware in addition to conversion module 50.

While the detailed drawings and specific examples given describe various exemplary embodiments, they serve the purpose of illustration only. It is to be understood that the invention is not limited in its application to the details of construction and the arrangements of components set forth in the preceding description or illustrated in the drawings. For example, the conversion module may measure CO2 concentration using various methods known in the art. Additionally, the same approach may be used for other gas concentration measurements that utilize mainstream or sidestream technology. Further, the module may be constructed in various shapes and sizes depending on the configuration of the patient monitor. Furthermore, other substitutions, modifications, changes, and omissions may be made in the design, operating conditions, and arrangements of the exemplary embodiments without departing from the scope of the invention as expressed in the appended claims.

What is claimed is:

1. A patient monitoring system, comprising:
   a patient monitor having a screen and a mainstream carbon dioxide input connector configured to receive a mainstream carbon dioxide concentration signal from a mainstream gas analyzer; and
   a sidestream gas analyzer having an output connector, the sidestream gas analyzer configured to transmit a sidestream carbon dioxide concentration signal via the output connector;
   wherein the patient monitor receives the sidestream carbon dioxide concentration signal via the mainstream carbon dioxide input connector for display on the screen.

2. The patient monitoring system of claim 1, wherein the patient monitor comprises logic used to convert the sidestream carbon dioxide concentration signal into a format suitable for display on the screen.

3. The patient monitoring system of claim 2, wherein the logic discerns whether a signal received via the mainstream carbon dioxide input connector is from the mainstream gas analyzer or the sidestream gas analyzer and converts the signal into data values for display on the screen accordingly.

4. The patient monitoring system of claim 1, wherein the sidestream carbon dioxide concentration signal comprises an end-tidal carbon dioxide gas concentration value.

5. The patient monitoring system of claim 4, wherein the patient monitor displays the end-tidal carbon dioxide value on the screen.

6. The patient monitoring system of claim 1, wherein the sidestream carbon dioxide concentration signal is displayed on the screen as a capnogram.

7. The patient monitoring system of claim 1, wherein the sidestream carbon dioxide analyzer further comprises:
   a sample tube adapted to convey a gas sample to the sidestream gas analyzer;
   a light source; and
   a photodetector used to measure attenuation of the light source in the gas sample.

8. The patient monitoring system of claim 7, wherein the sidestream carbon dioxide analyzer further comprises logic to create the sidestream carbon dioxide concentration signal in a sidestream signal format, wherein the sidestream signal format emulates a signal format of the mainstream carbon dioxide concentration signal.

9. The patient monitoring system of claim 1, wherein the sidestream carbon dioxide concentration signal is a digital signal.

10. The patient monitoring system of claim 1, wherein the output connector is directly plugged into the mainstream carbon dioxide input connector without an intervening cable.

11. A patient monitoring system, comprising:
    a patient monitor having a screen and a mainstream gas input connector configured to receive a mainstream gas concentration signal from a mainstream gas analyzer; and
    a sidestream gas analyzer having an output connector, the sidestream gas analyzer configured to transmit a sidestream gas concentration signal via the output connector;
    wherein the patient monitor receives the sidestream gas concentration signal via the mainstream gas input connector for display on the screen.

12. The patient monitoring system of claim 11, wherein the sidestream gas concentration signal comprises carbon dioxide concentration data.

13. The patient monitoring system of claim 12, wherein the patient monitor comprises logic used to convert the sidestream carbon dioxide concentration data into a format suitable for display on the screen.

14. The patient monitoring system of claim 13, wherein the logic discerns whether a signal received via the mainstream gas input connector is from the mainstream gas analyzer or the sidestream gas analyzer and converts the signal into data values for display on the screen accordingly.

15. The patient monitoring system of claim 12, wherein the sidestream carbon dioxide concentration data comprises an end-tidal carbon dioxide gas concentration value.

16. The patient monitoring system of claim 15, wherein the patient monitor displays the end-tidal carbon dioxide value on the screen.

17. The patient monitoring system of claim 12, wherein the sidestream carbon dioxide concentration data is displayed on the screen as a capnogram.

18. The patient monitoring system of claim 11, wherein the sidestream gas analyzer further comprises:
    a sample tube adapted to convey a gas sample to the sidestream gas analyzer;
    a light source; and
    a photodetector used to measure attenuation of the light source in the gas sample.

19. The patient monitoring system of claim 18, wherein the sidestream gas analyzer further comprises logic to create the sidestream gas concentration signal in a sidestream signal format, wherein the sidestream signal format emulates a signal format of the mainstream gas concentration signal.

20. The patient monitoring system of claim 11, wherein the sidestream gas concentration signal is an analog signal.

21. The patient monitoring system of claim 11, wherein the output connector is directly plugged into the mainstream gas input connector without an intervening cable.

22. A patient monitoring system, comprising:
    a patient monitor having a screen and an input connector configured to receive a mainstream carbon dioxide concentration signal from a mainstream gas analyzer; and a sidestream gas analyzer having an output connector, the sidestream gas analyzer configured to transmit a sidestream carbon dioxide concentration signal via the output connector, wherein a signal format for the mainstream carbon dioxide concentration signal is the same as a signal format for the sidestream carbon dioxide concentration signal and wherein the patient monitor receives the sidestream carbon dioxide concentration signal via the input connector for display on the screen.

23. The patient monitoring system of claim 22, wherein the patient monitor comprises logic used to convert the sidestream carbon dioxide concentration signal into a format suitable for display on the screen.

24. The patient monitoring system of claim 22, wherein the sidestream carbon dioxide concentration signal comprises an end-tidal carbon dioxide gas concentration value.

25. The patient monitoring system of claim 24, wherein the patient monitor displays the end-tidal carbon dioxide value on the screen.

26. The patient monitoring system of claim 22, wherein the sidestream carbon dioxide concentration signal is a digital signal.

27. The patient monitoring system of claim 22, wherein the output connector is directly plugged into the input connector without an intervening cable.

* * * * *